(12) United States Patent
Burns et al.

(10) Patent No.: US 6,584,805 B1
(45) Date of Patent: Jul. 1, 2003

(54) HOT BOTTLE INSPECTION APPARATUS

(75) Inventors: John William Burns, Westminster, CO (US); Dennis Ray Erickson, Arvada, CO (US); Jack Devin McKeehan, Conifer, CO (US); James Allen Gulka, Arvada, CO (US)

(73) Assignee: Coors Brewing Company, Golden, CO (US)

( * ) Notice: Subject to any disclaimer, the term of this patent is extended or adjusted under 35 U.S.C. 154(b) by 740 days.

(21) Appl. No.: 09/181,832

(22) Filed: Oct. 28, 1998

Related U.S. Application Data

(63) Continuation of application No. 08/831,384, filed on Apr. 1, 1997, now abandoned, and a continuation of application No. 08/898,535, filed on Jul. 22, 1997, now abandoned, which is a continuation of application No. 08/418,007, filed on Apr. 6, 1995, now abandoned, which is a continuation of application No. 08/111,115, filed on Aug. 24, 1993, now Pat. No. 5,437,702.

(51) Int. Cl.$^7$ .................................................. C03B 9/40
(52) U.S. Cl. .................... 65/29.12; 65/158; 65/160; 65/261; 209/524; 209/526; 264/40.1
(58) Field of Search ..................... 209/209, 523, 209/524, 525, 526; 65/29, 68, 158, 165, 160, 29.12, 261; 264/40.1

(56) References Cited

U.S. PATENT DOCUMENTS

| | | | |
|---|---|---|---|
| 4,019,819 A | | 4/1977 | Lodzinski .................... 356/73 |
| 4,691,830 A | * | 9/1987 | Ahl |
| 4,694,158 A | * | 9/1987 | Leser |
| 4,915,237 A | * | 4/1990 | Chang |
| 5,187,368 A | | 2/1993 | Galante et al. ............. 250/341 |
| 5,305,081 A | | 4/1994 | Gooch et al. ................ 356/240 |
| 5,510,621 A | | 4/1996 | Goldman ..................... 250/343 |
| 5,717,486 A | | 2/1998 | Burri et al. .................. 356/240 |
| 5,734,467 A | | 3/1998 | Lucas .......................... 356/240 |

OTHER PUBLICATIONS

"The Hand Book of Glass Manufacture" vol. II, Fay V. Tooley, published by Books For Industry, Inc. and the Glass Industry Magazine Division of Magazines for Industry, Inc. 1974, Library of Congress No. 74–77520, PPS 961–975.

U.S. patent application Ser. No. 08/914,984 filed Aug. 20, 1997 for "Hot Bottle Inspection Apparatus & Method" of Philip J. Lucas. TL6 2800 CP 4–4 L 24 Old eff date.

U.S. patent application Ser. No. 09/001,215 filed Dec. 30, 1997, for "Method for Inspecting Manufactured Articles" of Philip J. Lucas. old effective date.

(List continued on next page.)

*Primary Examiner*—John Hoffmann
(74) *Attorney, Agent, or Firm*—Klaas, Law, O'Meara & Malkin, P.C.; Michael A. Goodwin; William P. O'Meara

(57) ABSTRACT

A glass bottle production line comprising a bottle mold which has a plurality of mold cavities arranged in a predetermined order for forming bottles from glass parisons and for transferring the bottles to a conveyor in a predetermined sequence corresponding to the predetermined order of the mold cavities. The conveyor has a hot end portion and a cold end portion for receiving bottles from the bottle mold at an elevated temperature at the hot end portion and conveying the bottles to the cold end portion. A hot bottle inspector located at a fixed inspection station along the conveyor at the hot end portion non-touchingly inspects the bottles as the bottles are conveyed past the inspection station by the conveyor. A mold transfer signal and bottle detection signal are processed to determine the mold cavity used to produce the bottle detected at the inspector's station.

19 Claims, 5 Drawing Sheets

OTHER PUBLICATIONS

U.S. patent application Ser. No. 09/000,808 filed Dec. 30, 1997, for "Method for Inspecting Translucent Objects Using Imaging Techniques" of Philip J. Lucas. old effective date.

U.S. patent application Ser. No. 08/698,591 filed Sep. 24, 1998, for "Method for Measurement of Light Transmittance" of Hidalgo et al. old effictive date.

U.S. patent application Ser. No. 08/831,384 filed Apr. 1, 1997, for "Hot Bottle Inspection Apparatus and Method" of Burns, et al. This case.

U.S. patent application Ser. No. 08/898,766 filed Jul. 23, 1997, for "Method for Measurement of Light Transmittance" of Hidalgo et al. Old effective.

* cited by examiner

HOT BOTTLE INSPECTION APPARATUS

This application is a continuation of application Ser. No. 08/831,384 filed Apr. 1, 1997, now abandoned, and continuation of application Ser. No. number 08/898,535 filed Jul. 22, 1997, now abandoned. Application Ser. Nos. 08/831,384 and 08/898,535 are both continuations of application Ser. No. 08/418,007 filed Apr. 6, 1995, now abandoned, which is a continuation of application Ser. No. 08/111,115 filed Aug. 24, 1993, now U.S. Pat. No. 5,437,702. All of the above-referenced patent applications are hereby specifically incorporated by reference for all that is disclosed therein.

BACKGROUND OF THE INVENTION

The present invention relates generally to glass bottle production and, more particularly, to a glass bottle inspection apparatus adapted for use at the hot end of a glass bottle production line.

The manufacture of glass bottles begins with the preparation of raw materials. Sand and soda ash are measured in precise quantities, mixed together and conveyed to storage silos located over large melting furnaces. The mixed materials are continuously metered into the furnaces to replace molten glass which is dispensed from the furnaces after melting.

The furnaces are heated by a combination of natural gas and electricity and are operated at a temperature of over 2500 degrees Fahrenheit. The melted mixture of raw materials forms molten glass which flows from the furnaces through refractory channels, also known as forehearths, to a position over bottle forming machines.

A bottle forming machine known in the industry as an "I.S. machine" draws the glass into individual gobs and drops each gob into a blank mold. The blank mold forms a bottle preform, also referred to as a parison. The preform is transferred to a blow mold where it is blown by compressed air into a bottle. Each blow mold cavity typically contains indicia provided on a bottom wall thereof which embosses each bottle with code characters indicating the mold cavity in which it was formed.

The molds are lubricated by oil born carbon. The hot mold vaporizes the oil and some of the carbon immediately upon contact leaving most of the carbon deposited upon the mold. Thus, the area around the mold is an extremely dirty environment filled with oil and carbon vapors and condensate.

An I.S. machine typically has between six and sixteen individual sections, with each section having from one to four blow mold cavities. Each section may be capable of manufacturing one to four bottles at time. A typical eight section, triple gob, I.S. machine used in the production of beer bottles may produce 270 beer bottles per minute.

After the bottles have been blown, they are transferred from the respective blow mold cavities onto a moving conveyor belt. The bottles are positioned on the moving conveyor belt in a single line in a sequence corresponding to the sequence of the blow mold cavities in which the bottles were formed. The finished bottles transferred onto the conveyor from the blow mold are still red hot (approximately 1,000 degrees Fahrenheit). These hot bottles are conveyed by the conveyor belt through a hot end coating hood where they are chemically treated with a stannous chloride compound for strengthening. Vapors from the hot end coding hood also contribute significantly to the harsh environment found at the "hot end" of the bottle production line.

After passing through the hot end coating hood, the hot bottles are conveyed through an annealing oven or lehr where they are reheated and then cooled in a controlled manner to eliminate stresses in the glass. This annealing process typically takes from 20 to 30 minutes. The annealing process is the last process which takes place at the hot end of the production line. The portion of the production line downstream from the annealing oven is referred to as the "cold end" of the production line. In contrast to the hot end, the cold end is neither hot nor dirty. At the cold end of the production line, bottles are conveyed through a series of inspection devices. Typical prior art inspection devices include a squeezer which physically squeezes each bottle to check its sidewall strength. Another prior art cold end inspection device is referred to in the industry as a total inspection machine or T.I.M. which is sold by Emhart Glass having a business address of 123 Day Hill Road, Windsor, Conn. 06095. The total inspection machine physically engages each bottle and checks the size of the bottle neck opening and the thickness of the bottle sidewall and reads the code on the bottle bottom wall to determine the mold of origin. On a statistical sampling basis, The T.I.M. also sends bottles off line to be tested for burst strength, weighing, and measuring. Reports generated from the T.I.M. correlate bottle defects with the mold of origin. Another typical prior art inspection device is known as a "super scanner" sold by Inex, 13327 U.S. 19 North, Clearwater, Fla. 34624. The super scanner operates on each bottle on line. It initially scans a bottle, then engages and rotates the bottle approximately 90 degrees and scans it again. The super scanner uses image analysis to perform certain dimensional parameter checks of the bottle.

At both the T.I.M. and the super scanner inspection stations, defective bottles may be rejected by a cold end rejection device. After passing through the cold end inspection stations, bottles are transferred to a case packer machine, placed into a cardboard carton and conveyed to a palletizer machine for being placed in pallets. Loaded pallets are then shipped to a filling facility, such as a brewery.

A problem experienced with traditional glass bottle manufacturing operations as described above results from the fact that the bottle inspection stations are located at the cold end of the bottle production line. If a particular blow mold cavity begins producing defective bottles, e.g. as a result of a foreign object in the mold, the first defective bottle produced will not be detected until 30 to 40 minutes after its formation in the blow mold. As a result of this detection delay, the defective mold cavity will have continued to produce hundreds of defective bottles during the period between the first defective production and discovery of the first defective bottle. Furthermore, unless the defect is a defect of the type discovered by the T.I.M. machine which also identifies each bottle with a blow mold, the mold causing the problem will not be immediately apparent to the operator. As a result, the production operation must be shut down and each of the mold cavities of the I.S. machine must be inspected to detect the origin of the problem. Such shut down and inspection may be very time consuming and results in significant production loss in addition to the scrap produced by the defective mold cavity.

Prior to the present invention, it has been considered unworkable to place an inspection machine at the hot end of the bottle production line for a number of reasons: (1) as a result of the elevated temperature of the bottles at the hot end of the line, any engagement of the bottles by an inspection machine as is conventional with cold end inspectors would result in deformation of the bottle surface producing an ascetically unacceptable bottle; (2) the heat of the bottles at the hot end causes the bottles to glow and would thus make reading of mold origin indicating characters on the base of the bottle extremely difficult or impossible; (3) the contaminants in the atmosphere at the hot end of the line would coat the surface of any optical device used to image the bottles rendering imaging difficult or impossible; (4) the extreme heat and contamination at the hot end of the line would damage any electronics used on inspection devices positioned at the hot end.

SUMMARY OF THE INVENTION

The present invention is directed to a glass bottle production line which includes a bottle inspection apparatus located at the hot end of the line, contrary to the conventional wisdom in the art. The hot bottle inspection apparatus relies on non-touching inspection techniques and thus, does not damage the surface of the hot bottles. The inspection apparatus uses imaging assemblies which are shielded from the harsh environment at the hot end of the production line by a specially adapted housing assembly. Optical and electronic components positioned within the housing are cooled by a filtered cooling airflow provided within the housing. Clear panels in the housing wall enable imaging devices within the housing to image passing bottles without exposing the optics thereof to the harsh environment of the hot end. Fluid jets provided adjacent to these clear panels prevent contaminants from building up on the surface of the clear panels. The imaging data signals generated by the imaging devices are also used as detection signals to determine when a bottle has entered an inspection position on the conveyor. Monitoring signals from the I.S. machine and the bottle conveyor are processed along with the bottle detection signal by data processing apparatus to determine the mold of origin of each bottle which is being imaged, thus obviating the need to read indicia on the surface of a glowing bottle. Image data from each bottle is analyzed to determine whether or not the bottle is defective. A signal may be sent to a remote computer accessible to the operator. The remote computer has a display which indicates the mold of origin of each defective bottle. This information may also be stored by the computer for further analysis and/or display. As a result of this information which becomes available to the operator almost immediately after the production of a defective bottle, the operator may immediately identify the problem mold cavity and take corrective action. For example, the operator may simply disable the portion of the I.S. machine associated with production of defective bottles and correct the problem or, in the alternative, may terminate operation of the production line and immediately correct the problem with the identified mold cavity. In either case, production of scrap associated with the problem mold cavity is virtually eliminated and production line downtime is significantly reduced.

BRIEF DESCRIPTION OF THE DRAWING

An illustrative and presently preferred embodiment of the invention is shown in the accompanying drawing in which.

DETAILED DESCRIPTION OF THE INVENTION

Figure 1:
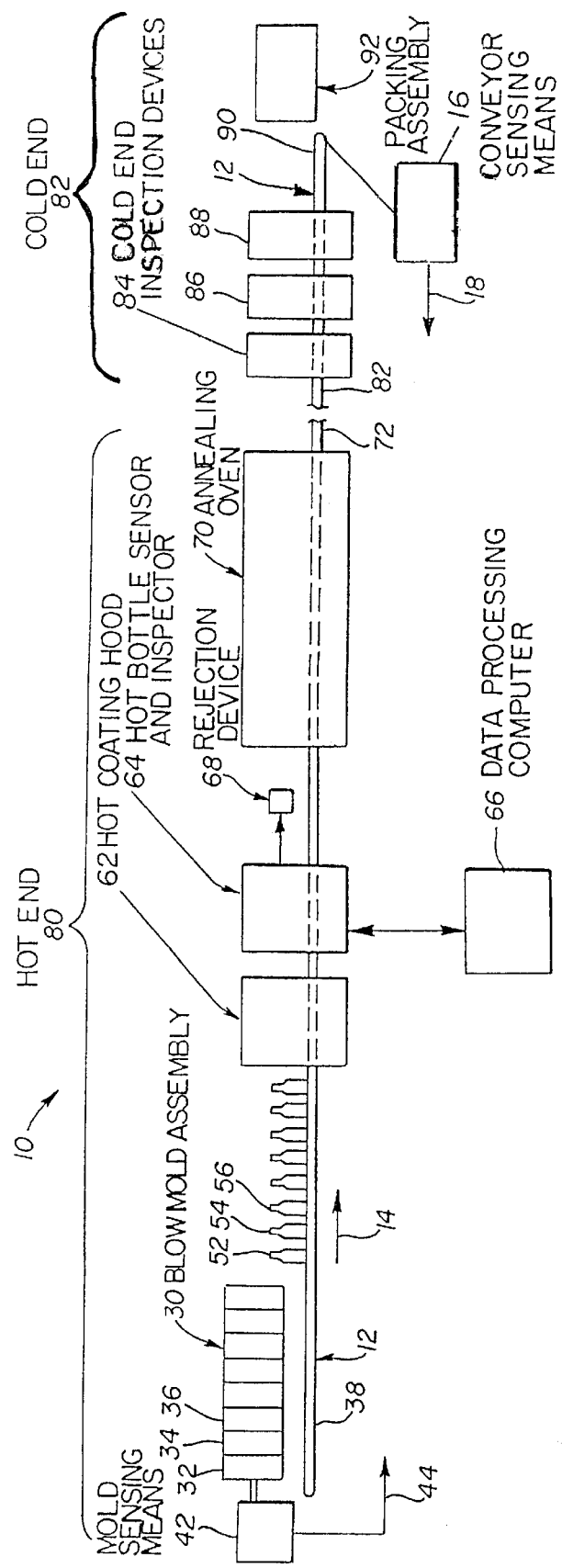
FIG. 1 is a schematic diagram of a glass bottle production line.

In general, as shown by FIG. 1, the invention may comprise a glass bottle production line 19 comprising bottle mold means 30 having a plurality of mold cavities 32, 34, 36 etc. arranged in a predetermined order for forming bottles 52, 54, 56 from glass parisons and for transferring the bottles to a conveyor means 12 in a predetermined sequence corresponding to the predetermined order of the mold cavities 32, 34, 36, etc. The conveyor means 12 has a hot end portion 80 and a cold end portion 82. The conveyor means receives the bottles from the bottle mold means 30 at an elevated temperature at the hot end portion 80 and conveys the bottles to the cold end portion 82. A hot bottle inspection means 64 is located at a fixed inspection station along the conveyor means 12 at the hot end portion 80 thereof. The hot bottle inspection means 64 non-touchingly inspects the bottles as the bottles are conveyed past the inspection station by the conveyor means 12. A mold monitoring device 42 is operatively associated with the blow mold assembly 30. Specifically, the mold monitoring device 42 generates a signal indicative of the operation of blow mold assembly 30. The hot bottle inspection means generates a signal indicative of the detection of a bottle at the inspector's station. A data processing assembly 66 processes the mold monitoring device signal and the bottle detection signal to determine the mold cavity which produced each bottle detected at the inspector's station, obviating the need to read indicia on the bottles. Mold cavity of origin information along with the results of inspection may be displayed on an operator readable device such as a cathode ray tube or paper printout to enable an operator to immediately identify a problem mold cavity and take corrective action. Having thus described the invention in general, further features of the invention will now be specifically described.

FIG. 1 is a schematic illustration of a glass bottle production line 10. The production line comprises a conveyor 12 which defines a bottle conveyance path. The conveyor moves bottles downstream in direction 14. A conveyor monitor assembly 16 (sometimes referred to herein as "conveyor sensing means") which may be, for example, a conventional electronic encoder mounted on a conveyor motor shaft, monitors the conveying movement of conveyor 12 and produces a conveyor displacement signal 18 representative thereof. In most bottle production lines the conveyor 12 is mechanically linked to the drive mechanism of the blow mold such that conveyor speed is always directly proportional to the speed of operation of the blow mold. In such a case any device which monitors mold displacement, for example, an incremental encoder mounted on the shaft of the mold drive unit, would also indicate conveyor displacement and is to be considered a conveyor monitor.

A blow mold assembly 30 comprises a plurality of mold cavity portions 32, 34, 36, etc. The blow mold assembly 30 may comprise a portion of a conventional I.S. machine. The blow mold assembly 30 is positioned at an upstream end 38 of conveyor 12. A mold monitor assembly 42 (sometimes referred to herein as a "mold sensing means") generates a mold transfer signal 44 (sometimes referred to herein as a "mold sensing signal" or a "mold signal") each time the blow mold 30 transfers bottles onto conveyor 12. Bottles 52, 54, 56, etc. are produced by mold cavity portions 32, 34, 36, etc. and are transferred to conveyor 12 in single file in a sequence corresponding to the sequence of their respective blow mold cavities of origin. The bottles 52, 54, 56 may be formed with indicia thereon indicative of the blow mold cavity of origin. The bottles 52, 54, 56, etc. are transferred onto the conveyor 12 at an elevated temperature which may be approximately 1000 degrees Fahrenheit such that the bottles are glowing.

A hot coating hood 62 is positioned at a station along the conveyor 12 a short distance downstream, e.g. 10 feet, from the blow mold 30.

A hot bottle inspection apparatus, also referred to herein as a hot bottle inspector 64, is positioned at a fixed station along the conveyor which may be a short distance, e.g. two feet, downstream from the hot coating hood 62. The hot bottle inspector 64 may thus be located in an extremely hot and dirty environment at the hot end 80 of the production line. A remote computer 66 removed from the harsh environment at the hot end of the production line is operably connected to the hot bottle inspector 64 and is-accessible to a production line operator. A rejection device 68 may be positioned immediately downstream from the hot bottle inspector 64 and is operable to remove bottles from the conveyor in response to commands from the hot bottle inspector 64.

An annealing oven 70 of a conventional type may be positioned downstream of the rejection device 68 and defines, at its downstream end portion 72, the terminal end portion of the "hot end" 80 of the bottle production line 10. In a typical production line used for producing glass beer bottles, the period of time elapsing from the transfer of a bottle onto the conveyor 12 by the blow mold 30 to the exit of that bottle from the downstream end 72 of annealing oven 70 may be thirty minutes.

The portion of the production line 10 located downstream of the annealing.oven exit 72 constitutes the "cold end" 82 of the production line. The cold end of the production line may comprise conventional cold end inspection devices 84, 86, 88 such as a squeezer, a T.I.M. machine, and a super inspector machine such as previously described in the "Background of the Invention" section of this application. The first of these cold end inspectors 84 may be positioned, e.g. 100 feet, downstream from the exit 72 of annealing oven 70. A conventional packing assembly 92, such as described above, may be provided downstream from the cold end inspection devices 84, 86, 88.

Figure 2:
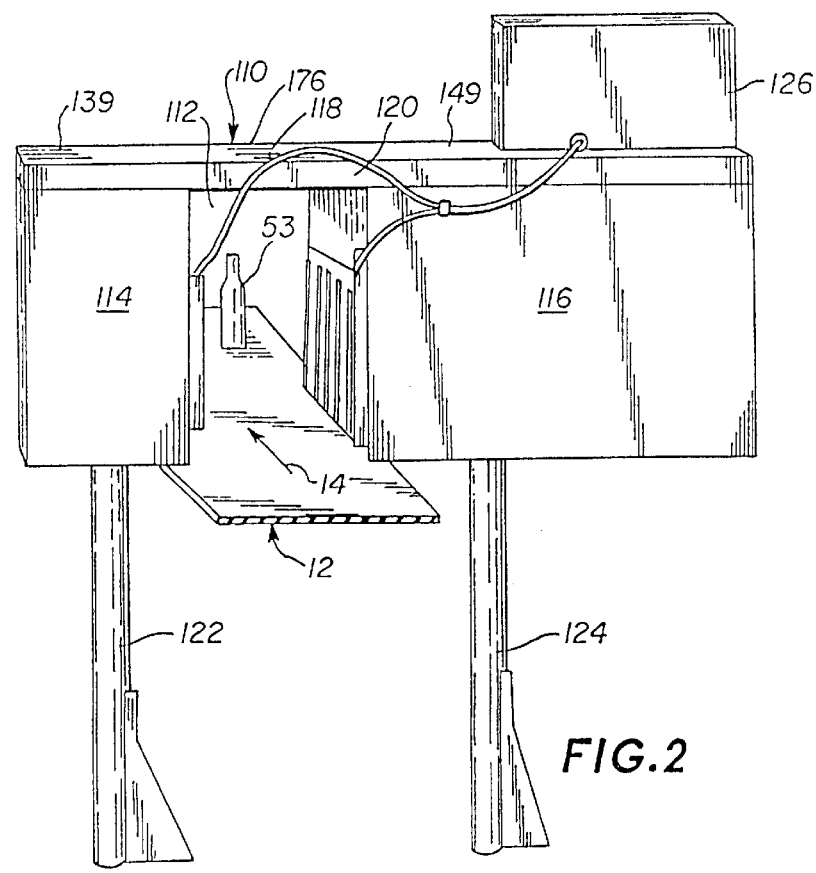
FIG. 2 is a perspective view of a hot bottle inspection apparatus and a portion of an associated conveyor belt.

As best illustrated by FIG. 2, the hot bottle inspection apparatus 64 comprises generally, a regular parallelepiped-shaped housing 110 with a generally inverted-U-shaped passage 112 in a central portion thereof dividing the housing into a first box-shaped portion 114, a second box-shaped portion 116 connected by a bridging portion 118. A first leg 112 is attached to the bottom of the first box portion and a second leg 124 is attached to the bottom of the second box portion enabling the housing to be positioned above a conveyor belt 12 with the inverted U-shaped opening 112 positioned immediately over the conveyor belt and enabling the passage of bottles 53, etc. therethrough. A filtered air supply assembly 126 is operably mounted on top of the second box portion 116 and provides a flow of filtered air through the interior portions of the housing as will be described in further detail below.

Figure 3:
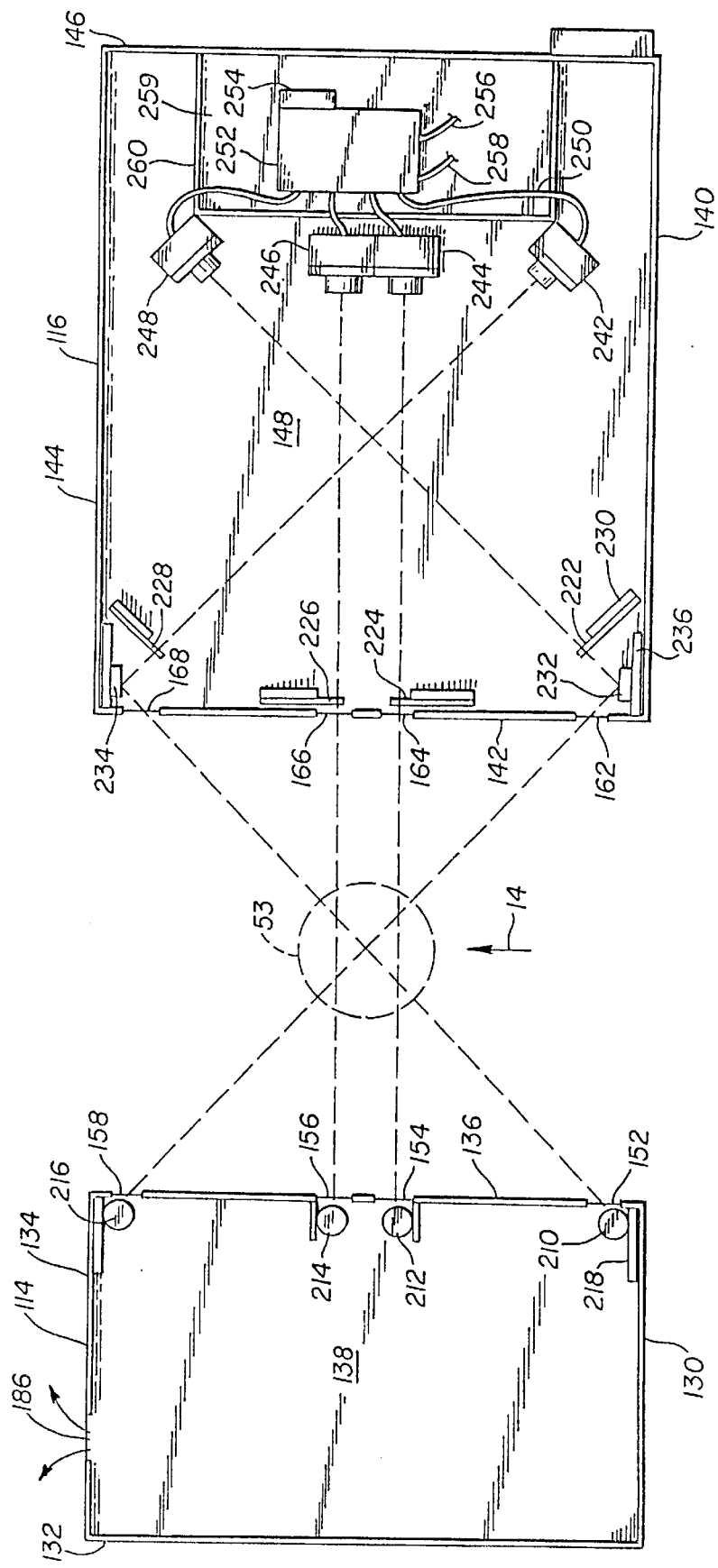
FIG. 3 is a cross-sectional top plan view of a hot bottle inspection apparatus.

FIG. 3 is a cross-sectional plan view of housing 110. As illustrated by FIG. 3, first box portion 114 comprises a front wall 130, a first side wall 132, a rear wall 134, a second side wall 136, a bottom wall 138 and a top wall 139 (FIG. 2). These housing walls may be constructed from sheet metal such as, for example, 0.090" thick stainless steel.

Second box portion 116 may comprise a front wall 140, a first side wall 142, a rear wall 144, a second side wall 146, a bottom wall 148, and a top wall 149 as illustrated in FIGS. 2 and 3.

Figure 4:
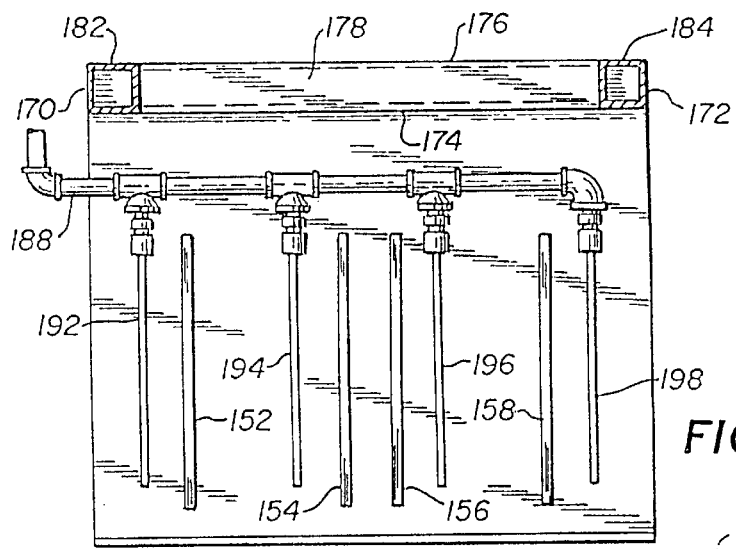
FIG. 4 is a partially cross-sectional elevation view of one face of the housing of a hot bottle inspection apparatus.

As best illustrated in FIGS. 3 and 4, first box second side wall 136 comprises four transparent panels 152, 154, 156 and 158, which may be high-strength, heat resistant, glass panels, mounted in sealing relationship over corresponding slots provided in side wall 136. Similarly second box side wall 142 has transparent panels 162, 164, 166, 168 sealingly positioned over slots in its side wall which are positioned opposite to the slots in side wall 136.

As best shown by FIGS. 2 and 4, bridge portion 118 comprises a front wall 170, a rear wall 172, a bottom wall 174 and top wall 176. These walls define a rectangular air passage 178 which ends at openings at the top of side walls 136 and 142 in first and second box portions 114, 116 placing the enclosure of first box portion 114 in fluid communication with the enclosure of second box portion 116. The bridge portion comprises first and second horizontal support members 182 and 184 that extend through the upper portions of the first and second box member and are attached thereto to provide structural rigidity to the housing.

An air inlet orifice (not shown) is positioned in the top wall 149 of the second box portion 116 to enable cool filtered air from the filtered air supply assembly 126 to enter the first box portion. An air discharge orifice 186, FIG. 3, may be provided near the bottom of side wall 114 and enables discharge of air therefrom. Except for these orifices, the housing may be sealed and thus air from the air supply assembly 126 enters the second box portion 116 and circulates therein, thereafter passes through air passage 178 into first box portion 114 and circulates therein and is finally discharged through orifice 186. In one preferred embodiment, the filter air supply assembly operates as follows: Plant compressed air is filtered and regulated to 100 psi by a Wilkerson #C040 2000 filter/regulator commercially available from Wilkerson Corp., P. O. Box 1237, Englewood, Colo. 80150. The pressurized air is then provided to an air cooler, such as a Vortec #780, which cools the air supplied to the interior of the housing and reduces the pressure to about 1 or 2 psi above atmospheric pressure. A second filter/regulator supplies 2–5 psi to the air jet tubes 192, 194, 196, 198 described below. The filters of the filter air supply assembly remove any contaminants from the air which is passed through the housing and the pressure of the supply assembly places the interior portions of the housing under a pressure slightly greater than atmospheric, preventing the infiltration of any contaminated air from outside the housing. The cooling air may have a temperature of approximately 60 degrees Fahrenheit when it enters the housing and may be provided at a flow rate of approximately 35 cubic feet per second for a housing having a total interior volume of approximately 10 cubic feet.

A pressurized air conduit 188 is operably connected to the filtered air supply 126 and provides pressurized air to air jet tubes 192, 194, 196, 198 associated with transparent panels 152, 154, 156, 158. Air jets produced by these tubes prevent the build-up of contamination on the transparent panels in the harsh environment in which the inspection apparatus is located. Similar air jet tubes are associated with the transparent panels 162, 164, 166, 168 of the second box portion 116 and are supplied with pressurized air from the filtered air supply unit 126. In an alternative embodiment (not shown), a transparent glass cover panel is positioned over each transparent panel 152, 154, 156, 158 via quick release mechanisms that allow the cover panels to be quickly removed, cleaned and reinstalled.

Fluorescent bulbs 210, 212, 214, 216 mounted on supports 218, etc. attached to the housing are positioned opposite each of the transparent panels 152, 154, 156, 158 of the first box portion 114. The fluorescent bulbs extend the full length of each of the transparent portions and provide light used to image bottles passing through the inspection apparatus. Collimating lenses, which may comprise conventional Fresnell lenses 222, 224, 226, 228 are mounted on supports 230, etc. within the second box portion of the housing, as illustrated in FIG. 3.

Figure 5:
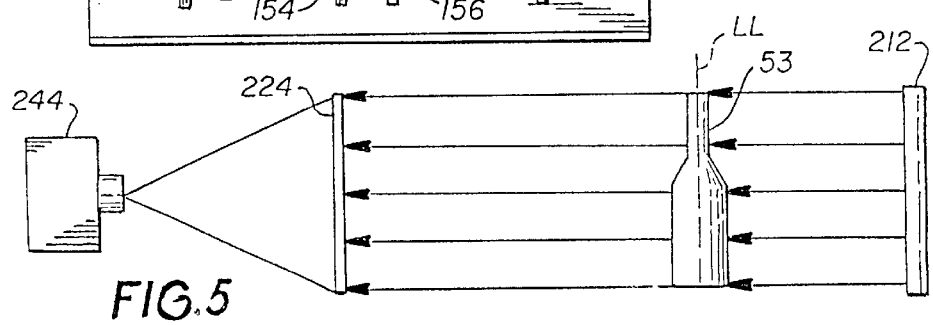
FIG. 5 is a schematic diagram illustrating certain optical components used to image a glass bottle.

A first and second mirror 232, 234 are positioned adjacent transparent panels 162, 168 and are mounted on supports 236, etc. attached to the walls of housing second box portion 116. Image sensors 242, 244, 246, 248 are mounted in second box portion 116 as illustrated in FIG. 3. The image sensors may comprise Model RL0258G available from EG & G Reticon, 2260 Landmeier Road, Suite J, Elk Grove Village, Ill. 60007-2693. Each image sensor is connected by conventional cables 250 etc. to a central data processor 252 mounted within the second box portion 116. The central data processor 252 may have an input device 254, such as a key pad physically mounted thereon. In a preferred embodiment, the central data processor 252 may also receive programming input as well as send process data to a remote computer 66 to which it is connected by conventional cables 256. The central data processor 252 may also be connected to send commands to a conventional bottle rejection device 68 by conventional cables 258. In one preferred embodiment of the invention, the central data processor 252 is positioned within a separately sealed interior cavity 259 provided by interior wall 260 which separates it from the remainder of second box portion 116 of the housing. In this embodiment, wall 146 of the housing comprises a hinged door 262. The cavity 259 in which the central data processor 252 is located may have a separate inlet (not shown) connecting it with the filtered air supply 126 and may further comprise a separate air discharge outlet (not shown). The separate cavity enclosing the central data processor 252 thus receives a cooling filtered airflow therethrough. However, if the door 262 must be opened during operation in the harsh environment, contaminants which may enter the chamber in which the central data processor 252 is located will be prevented from entering the portion of the enclosure containing the various optical components. The center line of beams of light from the illumination sources which pass through a bottle and thence, through the collimating filters to the various imaging devices, are illustrated by dash lines in FIG. 3. The general operation of a collimating lens in passing only parallel rays of light is illustrated schematically in FIG. 5.

The general technique of imaging of bottles onto photoelectric devices such as CCD's (charge coupled devices) and the subsequent analysis of the data signal to measure various bottle parameters is well known in the art. In one preferred embodiment of the present invention, the particular physical parameter of the bottle which is determined by the imaging/ data analysis process is the diameter of the bottle at various predetermined positions along the central longitudinal axis LL of the bottle. In one preferred embodiment 16 such diameter measurements are made per imaging device per bottle. It will be seen from FIG. 3 that the bottle is viewed from four different perspectives and thus, any deviation in bottle diameter which might be hidden by viewing the bottle from a single perspective is clearly detected by this multiple perspective arrangement. Thus, the need to rotate the bottle is obviated.

The measured bottle parameters may be compared with predetermined values and any bottle having parameters exceeding a fixed tolerance from this value are determined by the system to be defective. In another embodiment, rather than using fixed tolerances, the bottles are allowed to vary from a predetermined value by a variable tolerance amount. The value of this variable tolerance at any particular time is dependent upon a standard deviation value which is calculated using normal statistical methods based upon measurement of the subject parameter taken from a pre-set number of immediately preceding bottles, e.g. 256 bottles.

Figure 6:
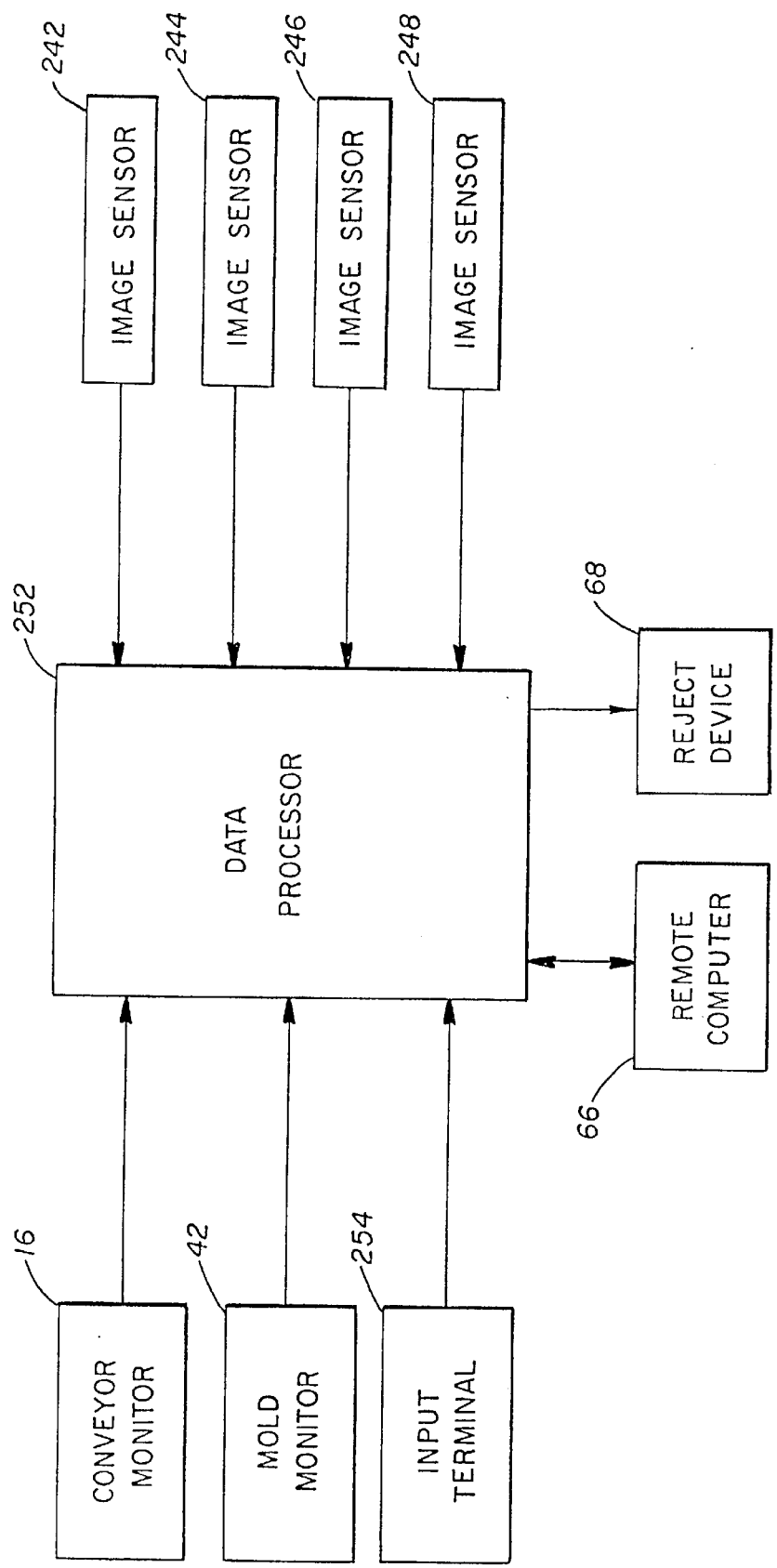
FIG. 6 is a block diagram of a sensing and control assembly for a hot bottle inspection apparatus.
Figure 7:
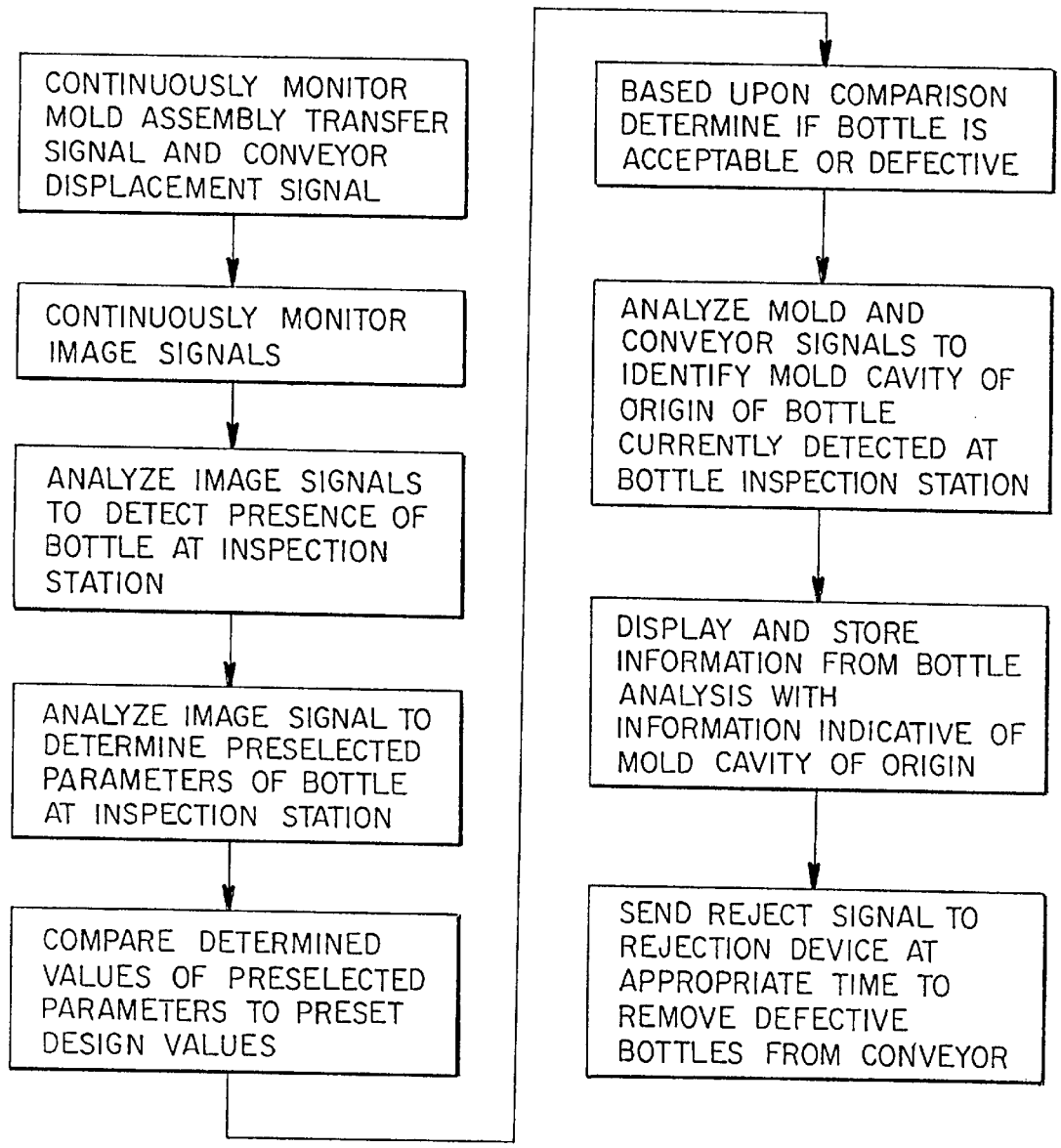
FIG. 7 is a diagram of basic operations performed by the sensing and control assembly of FIG. 6.

The basic control components used in bottle inspection and the basic method of operation of those components are as illustrated in FIGS. 6 and 7. As shown by FIG. 6, the system's central data processor 252 receives and processes image signals from each of the four sensor devices 242, 244, 246, 248. As previously mentioned, the image sensors may be conventional CCD based sensors. The data processor 252 also receives and processes signals from conveyor monitor 16 and mold monitor 42. In this manner, the data processor 252 is operatively connected to the devices 242, 244, 246, 248, the conveyor monitor 16 and the mold monitor 42. In order to re-program certain software features of the data processor, an input terminal 254 is provided which may be, for example, a key pad mounted within housing 110. In the alternative, the data processor 252 may be provided with a remote input terminal such as a remote computer 66. In addition to functioning as an input device, the remote computer 66 may also function as a display and data storage device for displaying information to the operator such as a history of the number of bottle rejects in a particular run, as well as the mold cavity of origin associated with each of the defects. As further shown by FIG. 6, the data processor may provide a signal to reject device 68 for removing defective bottles from the conveyor line. A separate control panel display (not shown) may also be mounted within housing 210 adjacent to input terminal 254 to enable direct viewing of information by an operator at the inspection station. Such a display could be a conventional LCD display. The data processor 252 may comprise hard-wired electronic components or may comprise one or more microprocessors which perform the various computational tasks in software or firmware or the data processor 252 may comprise a combination of such electronic components and programmable microprocessors.

The basic operations performed by the data processor 252 are as illustrated in FIG. 7. Based upon the mold monitor signal 44 and the conveyor monitor signal 18 which it receives, the data processor 252 continuously monitors the operating cycle of the mold and the displacement of bottles by the conveyor after each mold transfer of bottles to the conveyor. The data processor also continuously monitors the signals from image sensors 242, 244, 246, 248. It uses these image signals to detect the presence or absence of a bottle at the inspection station and, thus, the image sensors may be referred to herein as "bottle sensors" or "bottle detectors" and the signals produced by the image sensors may be referred to herein as "bottle sensing signals" or "bottle detection signals". It also analyzes the image signals to determine the values of certain pre-selected bottle parameters. In one embodiment, the parameters comprise a series of diameter measurements at predetermined positions along the bottle central longitudinal axis. The data processor compares these determined values of pre-selected bottle parameters to preset design values. If all of the determined values fall within a preset tolerance of the preset design values, then the bottle is determined to be acceptable. If any of the determined values fall outside of the preset tolerance for that value, then the bottle is determined to be defective. In addition to using a fixed tolerance value, variations in tolerance may be built in into the acceptability determination based upon a statistical sampling of previously inspected bottles to account for fluctuations due to slight differences in materials, operating conditions, etc. The mold and conveyor signals are analyzed to determine the mold cavity of origin of the bottle which is currently detected at the bottle inspection station. This information is displayed and stored along with the information from the bottle analysis so as to indicate the mold cavity of origin of each defective bottle and to further identify the parameter deviation which was the source of the rejection determination. This information may be displayed on a display screen (not shown) provided within the housing 110 and accessible to an operator through back panel 146 and/or may be provided on the display screen of remote computer 66. In response to each determination of a defective bottle, a rejection signal may be sent to actuate a rejection device 68 such as a conventional air jet rejection device which is operated at an appropriate time based upon conveyor speed to remove a defective bottle as it passes.

In the above described embodiment the determination of the cavity of origin of a bottle is based upon conveyor displacement occurring after a mold cavity transfer signal, i.e., since each bottle must travel a know conveyor distance after it is transferred to the conveyor by the blow mold, each mold cavity may be assigned a predetermined distance value measured in conveyor encoder pulses. Thus, by counting the number of conveyor encoder pulses occurring after the mold transfer signal and comparing this count to the predetermined distance values the particular mold cavity which produced the bottle currently at the inspector's station may be determined. Alternatively, the bottle/mold cavity determination could be a time-based system rather than a distance-based system. For example, in such a time-based system, at system start-up the number of clock pulses occurring between the first mold transfer signal and the first bottle detection could be stored as a time value to be associated with the first mold cavity. Clock pulse time values would also be stored for each succeeding bottle/mold cavity from the first mold transfer upon the detection of subsequent bottles. Thereafter, after each mold transfer signal, these stored time values, with appropriate tolerances, would be compared to current clock pulse counts to associate each bottle detected with its respective mold cavity. If the operating speed of the line were changed, these initially stored time values would be changed proportionately. For example, if at the initial start-up speed the first mold cavity time value were 10,000 clock pulses and if the line speed of the blow mold/conveyor system were subsequently doubled, then the first mold cavity time value would be adjusted by dividing the original time value by 2, i.e., it would be 5,000 clock pulses at this subsequent higher operating speed. Thus, in this embodiment, monitor assembly 16 may comprise a clock unit rather than a distance encoder. In a slight modification to the above described time-based system, the time between mold machine transfer pulses is divided into equal length intervals or "windows" based upon the number of mold cavities in the mold machine. The system then correlates bottles to mold cavities based upon the particular time window in which a bottle is sensed. The occurrence or each time window is determined by counting clock pulses after a mold transfer signal. Windows are shortened or lengthened in accordance with variations in line speed.

It is contemplated that the inventive concepts herein described may be variously otherwise embodied and it is intended that the appended claims be construed to include alternative embodiments of the invention except insofar as limited by the prior art.

What is claimed is:

1. A glass bottle production line comprising:

a) a bottle mold assembly;

b) a conveyor having a hot end portion positioned proximate said bottle mold assembly and a cold end portion positioned remotely from said bottle mold assembly;

c) a hot bottle inspector comprising a bottle imager located at a fixed inspection station along said conveyor at said hot end portion thereof and a pressurized housing disposed in enclosing relationship with said imager;

d) a mold monitor assembly operatively associated with said bottle mold assembly; and e) a data processor operatively connected to said mold monitor assembly and said bottle imager.

2. The bottle production line of claim 1, wherein:

said bottle mold assembly has a plurality of mold cavities arranged in a predetermined order; and said pressurized housing has a flow of clean air therethrough.

3. The bottle production line of claim 2 wherein said bottle mold assembly is adapted to form bottles from glass parisons and transfer said bottles to said conveyor in a predetermined sequence corresponding to said predetermined order of said mold cavities and said imager is adapted to non-touchingly, imagingly inspect said bottles as said bottles are conveyed past said inspection station by said conveyor.

4. The bottle production line of claim 2 wherein said pressurized housing includes at least one transparent portion therein.

5. The bottle production line of claim 4 wherein said pressurized housing includes:

at least one air jet tube connected to a source of pressurized air; and wherein said at least one air jet tube is located adjacent said at least one transparent portion.

6. The bottle production line of claim 5 wherein said pressurized housing defines a housing interior located within said housing and a housing exterior located outside of said housing, said pressurized housing includes at least one external surface facing said housing exterior and said at least one air jet tube is located in said housing exterior adjacent said at least one housing external surface.

7. The bottle production line of claim 2 wherein:

said pressurized housing defines a housing interior located within said pressurized housing and a housing exterior located outside of said pressurized housing;

said housing interior contains an internal atmosphere;

said housing exterior defines an external atmosphere;

said internal atmosphere is at a higher pressure than said external atmosphere; and said imager is exposed to said internal atmosphere.

8. A glass bottle production line comprising:

a) a bottle mold assembly;

b) a conveyor having a hot end portion positioned proximate said bottle mold assembly and a cold end portion positioned remotely from said bottle mold assembly; and c) a hot bottle inspector comprising a bottle imager located at a fixed inspection station along said conveyor at said hot end portion thereof and a pressurized housing disposed in enclosing relationship with said imager;

wherein, said pressurized housing defines a housing interior located within said pressurized housing and a housing exterior located outside of said pressurized housing;

wherein, said housing interior contains an internal atmosphere;

wherein, said housing exterior defines an external atmosphere;

wherein, said internal atmosphere is at a higher pressure than said external atmosphere; and wherein, said imager is exposed to said internal atmosphere.

9. The bottle production line of claim 8 further comprising:

a) a mold monitor assembly operatively associated with said bottle mold assembly; and b) a data processor operatively-connected to said mold monitor assembly and said bottle imager.

10. The bottle production line of claim 8, wherein:

said bottle mold assembly has a plurality of mold cavities arranged in a predetermined order; and said pressurized housing has a flow of clean air therethrough.

11. The bottle production line of claim 10 wherein said bottle mold assembly is adapted to form bottles from glass parisons and transfer said bottles to said conveyor in a predetermined sequence corresponding to said predetermined order of said mold cavities and said imager is adapted to non-touchingly, imagingly inspect said bottles as said bottles are conveyed past said inspection station by said conveyor.

12. The bottle production line of claim 10 wherein said pressurized housing includes at least one transparent portion therein.

13. The bottle production line of claim 12 wherein said pressurized housing includes:

at least one air jet tube connected to a source of pressurized air; and wherein said at least one air jet tube is located adjacent said at least one transparent portion.

14. The bottle production line of claim 13 wherein said pressurized housing includes at least one external surface facing said housing exterior and said at least one air jet tube is located in said housing exterior adjacent said at least one housing external surface.

15. A glass bottle production line comprising:

a) a bottle mold assembly;

b) a conveyor having a hot end portion positioned proximate said bottle mold assembly and a cold end portion positioned remotely from said bottle mold assembly;

c) a hot bottle inspector comprising a bottle imager located at a fixed inspection station along said conveyor at said hot end portion thereof and a pressurized housing disposed in enclosing relationship with said imager;

d) a mold monitor assembly operatively associated with said bottle mold assembly; and e) a data processor operatively connected to said mold monitor assembly and said bottle imager;

said pressurized housing defines a housing interior located within said pressurized housing and a housing exterior located outside of said pressurized housing;

said housing interior contains an internal atmosphere;

said housing exterior defines an external atmosphere;

said internal atmosphere is at a higher pressure than said external atmosphere; and said imager is exposed to said internal atmosphere.

16. The bottle production line of claim 15 wherein said mold monitor assembly is adapted to generate a mold signal indicative of placement of hot bottles on said conveyor by said bottle mold assembly, said bottle imager is adapted to generate a bottle sensing signal indicative of the detection of a bottle at said inspection station; and said data processor is adapted to process said mold signal and said bottle sensing signal to determine the mold cavity used to form the bottle detected at said inspection station.

17. The bottle production line of claim 15 wherein said pressurized housing includes at least one transparent portion therein.

18. The bottle production line of claim 17 wherein said pressurized housing includes:

at least one air jet tube connected to a source of pressurized air; and wherein said at least one air jet tube is located adjacent said at least one transparent portion.

19. The bottle production line of claim 18 wherein s aid pressurized housing includes at least one external surface facing said housing exterior and said at least one air jet tube is located in said housing exterior adjacent said at least one housing external surface.

* * * * *